United States Patent [19]

Ehrenthal et al.

[11] 4,208,482

[45] Jun. 17, 1980

[54] IMMOBILIZATION OF GLUCOSE ISOMERASE

[75] Inventors: Irving Ehrenthal, University City; Keith E. Miner, Mehlville, both of Mo.

[73] Assignee: Anheuser-Busch, Incorporated, St. Louis, Mo.

[21] Appl. No.: 679,769

[22] Filed: Apr. 23, 1976

[51] Int. Cl.² .................. C07G 7/02; C12D 13/04
[52] U.S. Cl. .................................... 435/178; 435/94
[58] Field of Search .............. 195/31, 31 F, 63, 68, 195/DIG. 11, 66 R

[56] References Cited

U.S. PATENT DOCUMENTS

| | | | |
|---|---|---|---|
| 3,779,869 | 12/1973 | Zienty | 195/68 |
| 3,834,988 | 9/1974 | Shieh et al. | 195/66 R |
| 3,843,442 | 10/1974 | Moskowitz | 195/68 X |
| 3,956,065 | 5/1976 | Idaszak et al. | 195/31 F |

OTHER PUBLICATIONS

Toda et al., Sucrose Inversion by Immobilized Yeast Cells in a Complete Mixing Reactor Biotechnology and Bioengineering, vol. XVII 1975, (pp. 481-497).
Strandberg et al., Free and Immobilized Glucose Isomerase from *Streptomyces phaeochromogenes*, Applied Microbiology, vol. 21, No. 4, 1971 (pp. 588-593).
Nilsson et al., The Use of Bead Polymerization of Acrylic Monomers for Immobilization of Enzymes Biochimica et. Biophysics Actz, vol. 268, 1972 (pp. 253-256).

*Primary Examiner*—David M. Naff
*Attorney, Agent, or Firm*—Gravely, Lieder & Woodruff

[57] ABSTRACT

Immobilized glucose isomerase is prepared by mixing 0.5 to 1.5 parts by weight whole microbial cells containing glucose isomerase with one part by weight agar, combining the resultant mixture with an organic solvent, recovering discrete particles of agar gel with the whole microbial cells entrapped therein and drying the agar gel particles. The immobilized glucose isomerase has long half life stability when used in a column in a continuous process to convert glucose to fructose.

8 Claims, No Drawings

IMMOBILIZATION OF GLUCOSE ISOMERASE

BACKGROUND OF THE INVENTION

This invention relates to immobilized enzymes, a process for preparing such immobilized enzymes, and the use of such immobilized enzymes to convert glucose to fructose in a continuous column process.

In conventional enzyme conversion processes, the enzymatic reaction is conducted by mixing the enzyme with the substrate, and thereafter removing the enzyme from the products or the unreacted substrate following the reaction. The difficulty in separating or recovering used enzymes has continued to be a problem. Because of the relatively high cost of enzymes, it is desirable to recover them for re-use in subsequent reactions.

Procedures for carrying out this recovery of enzyme for re-use are impractical for water soluble enzymes; recovery of whole cell enzyme is generally relatively costly and not worthwhile because of loss of significant amounts of activity in the initial isomerization.

In the conversion of glucose to fructose using glucose isomerase, because of the economics involved in producing glucose isomerase, it is of the utmost importance to use the isomerase under conditions whereby maximum yields of fructose are produced using minimum quantities of glucose isomerase. Moreover, the conditions for isomerizing should be such that minimal quantities of objectionable by-products are produced.

Various microorganisms are known in the art which produce glucose isomerase. For example, *Pseudomonas hydrophila*, microorganisms classified as belonging to the Streptomyces genus, such as *Streptomyces flavovirens, Streptomyces achromogenes, Streptomyces echinatus* and *Streptomyces albus, Aerobacter cloacae, Bacillus megaterium, Acetobacter suboxydans, Acetobacter melanogenus, Acetobacter roseus, Acetobacter oxydans, Bacillus fructose* and *Lactobacillus fermenti* are known to produce glucose isomerase.

This application is particularly concerned with use of organisms of the Actinoplanes genus, specifically *Actinoplanes missouriensis*, to produce glucose isomerase. This is broadly shown in Shieh et al U.S. Pat. No. 3,834,988.

Glucose isomerase is produced predominantly intracellularly by a number of the foregoing microorganisms. Thus, the major portion of the glucose isomerase is found within the cell walls of the microorganisms. Normally when these cells are used to isomerize glucose to fructose in a batch process, some loss in enzyme activity ensues and the recovery of the cells from the product for re-use of the enzyme is difficult as well as costly.

In answer to these problems, the art has developed immobilized enzymes, in which the enzymes are bound to inert or insoluble carriers and these immobilized enzymes can be used in columns to produce continuous reactions in which conversion of glucose to fructose takes place continuously in the column.

In certain cases it is advantageous to use an immobilized enzyme rather than a soluble one. The advantages of using an immobilized enzyme in comparison with one in soluble form are that the immobilized enzyme is re-usable and does not contaminate the reaction products and, therefore, is eminently suitable for continuous or repeated use. The disadvantages of the known immobilized enzymes are that some have to be prepared by rather complicated methods and, accordingly, are relatively expensive, and others require a rather large proportion of a carrier or a binder. Also some of the known immobilized enzymes suffer from the disadvantage that when packed in a column they exhibit flow properties which are not satisfactory. Moreover, a great many of the known binders are synthetic polymer products and consequently, are not suitable for production of foodstuffs.

In an article entitled "Sucrose Inversion by Immobilized Yeast Cells in a Complete Mixing Reactor" by Toda and Shoda, published in *Biotechnology and Bioengineering*, Vol. XVII, pages 481–497 (1975) a method of preparing a spherical agar gel is disclosed. In this process a suspension of yeast cells having invertase activity is mixed into a 2.5% (w/v) agar solution at 50° C. The volume ratio of the yeast cell suspension to the agar solution is 1:4. The resulting mixture is then injected into a cold solution of toluene and tetrachloroethylene in a vertical glass tube to produce gelatinized agar pellets. The pellets were spherical and yeast cells were distributed homogeneously in the pellets.

In Zienty U.S. Pat. No. 3,779,869, a process for stabilizing glucose isomerase in whole bacterial cells is disclosed. This process comprises treating whole bacterial cells having a glucose isomerase activity at a pH from about 6.5 to about 8.5 with from about 0.1 to about 50 weight percent glutaraldehyde (based on the dry weight of the cells). However, Zienty's process results in a product suitable only for a batch process. The flow properties of the bacterial cells prevent their use in a continuous system by themselves.

In O'Driscoll et al U.S. Pat. No. 3,859,169, an enzymatically active soluble gel is formed by polymerizing to a gel a reaction mixture containing water, a water-soluble polymerizable monomer (a glycol unit), a cross-linking agent, a synthetic polymer, a free radical initiating system, and an enzyme. However, O'Driscoll did not employ glucose isomerase in his polymerized gel. Moreover, there is no mention in this patent of the use of whole cell glucose isomerase.

Moscowitz U.S. Pat. No. 3,843,442 shows immobilized glucose isomerase prepared by reacting whole microbial cells containing glucose isomerase with a diazotized aromatic primary diamino compound. This reaction is relatively complex and results in a substantial loss of activity.

Republic of South Africa application No. 73/5916 by Amotz shows immobilized glucose isomerase prepared by combining enzyme, reinforcing agent (if desired), cross-linking agent, water and/or organic solvent(s). Amotz does not disclose or claim an entrapped enzyme.

Thompson U.S. Pat. Nos. 3,788,945 and 3,909,354 disclose processes of enzymatically converting glucose to fructose by passing a glucose-containing solution through a bed of glucose isomerase which has been released from the cell and then bound to an inert carrier described in diethylaminoethyl cellulose and other porous synthetic anion-exchange resins.

Accordingly, it is the principal object of the present invention to provide a continuous process for enzymatically isomerizing glucose to fructose. A continuous system is more efficient, and consequently less expensive, than a batch system.

Another object is to provide a whole cell glucose isomerase entrapped in agar for use in a continuous process of converting glucose to fructose.

Another object is to provide a method for producing this agar entrapped whole cell glucose isomerase by means of a relatively simple process.

Still another object is to provide the aforementioned immobilized glucose isomerizing enzyme having a half life substantially longer than the half life of known non-immobilized whole cell glucose isomerizing enzymes.

A further object is to provide a method of immobilizing glucose isomerase in spherical agar particles in combination with cobaltous ions, whereby the activity of the enzyme is enhanced without the need for using cobaltous ion in the substrate.

These and other objects and advantages will become apparent hereinafter.

SUMMARY

This invention relates to immobilized glucose isomerase and to a process of preparing same in which the immobilization is effected by means of entrapping whole cell glucose isomerase in spherical particles of agar gel. This invention utilizes a high ratio of glucose isomerase to agar gel so that fewer particles are required per unit of fructose production. Also the half life stability of the ajar gel-Actinoplanes enzyme is longer than that of other known non-immobilized whole cell glucose isomerase systems. This invention also relates to a process for producing a novel glucose isomerase entrapped in agar gel and a process for producing fructose from glucose in a column by means of a continuous flow process using the spherical gel particles of glucose isomerase and agar.

DETAILED DESCRIPTION

In preparing the product of this invention, whole cell enzyme is entrapped in a natural hydrocolloid, specifically agar, to produce generally spherical agar gel particles which can be advantageously used in a continuous column reactor system. The whole cell enzyme may be derived from organisms of the Actinoplanes genus, preferably from *Actinoplanes missouriensis* or other organisms. The entrapment process of this invention is a simple one. Variations of this process render it possible to retain most of the original enzyme activity. Other known methods of immobilization of glucose isomerase often result in significant losses in enzyme activity.

Cobalt salts are known to enhance the activity of glucose isomerase. The immobilized whole cell enzyme preparation should preferably contain 50 to 100 ppm of cobaltous ion (based on dry cell weight). This level may be attained in either of two ways:

(1) The glucose isomerizing organism may be grown in a medium containing 0.05 to 0.5 micromoles of cobaltous ion, or
(2) A cobalt salt may be added to the whole cell suspension, grown in the absence of added cobalt, prior to mixing with agar in the immobilization process.

Either of these procedures allows for elimination of the use of cobaltous ion in the glucose-containing substrate used in the continuous isomerization process, while still retaining adequate enzyme activity.

The spherical agar particles of entrapped enzyme are 0.15 to 2.5 mm in size. The whole cell enzyme is distributed homogeneously throughout each particle. These gel particles are suitable for packing in a column and the isomerase reacts with the glucose syrup which is passed through the column to produce a glucose-fructose syrup from the column.

The half life of the enzyme (or the time it takes for the enzyme to lose one-half of its activity) is substantially greater than that presently known for non-immobilized whole cell glucose isomerase. The half life is at least about 15 days, and preferably 24 or more.

The use of a column allows continuous processing of the glucose syrup and efficient use of the entrapped enzyme. The column height may be about 3 feet to about 40 feet and the diameter may be about 1 foot to about 14 feet. The retention time may be from 0.5 to 4.0 hours. The temperature may be 55° C. to 70° C., preferably 60° C. to 65° C.

Using this procedure the product from the column is 42 to 53% fructose and 50 to 45% dextrose from a 92 to 100% dextrose feed.

Following are more specifics of the preparation and use of the agar entrapped glucose isomerase of this invention.

Agar is the dried extract from several species of red algae. It is a mixture of galactose polysaccharides consisting of neutral agarose and sulfated galactan. It forms a strong gel which is resistant to disintegration at temperatures below 95° C. Agar has found wide use in food products. These properties of agar permit it to be used as a carrier support or matrix for the immobilization of glucose isomerase.

The agar is dissolved in boiling water with agitation. This stirred solution is then cooled and maintained at about 50° C. to about 65° C. The whole cell glucose isomerase is dispersed in water at ambient temperature. This enzyme suspension is then added to the agar solution and mixed in a manner so as to maintain a temperature between 45° C. and 60° C. The ratio by weight of agar to whole cells is generally 1 part agar to 0.5–1.5 parts of whole cells. The preferred ratio is 1 part agar to 1 part of whole cells.

The mixture is then injected into a suitable organic solvent at a temperature of 5° C. to 15° C. to form the gel particles. Gentle agitation is used to prevent coalescence. One solvent system is comprised of ethyl acetate and ethylene dichloride in a 3:1 ratio (by volume). Particles can also be prepared by using ethyl acetate alone. The solvent is then decanted and the gel particles are washed with water to remove any adhering solvent. The washed gel particles are then dried to a moisture level of about 5 to about 15%, preferably 5 to 10%.

In a modification of our basic process the whole cell enzyme suspension is treated with a bifunctional alkyl cross-linking reagent, preferably glutaraldehyde, before being added to the agar solution. The glutaraldehyde level can range from 1–10% of the weight of the dry whole cells. The preferred level is 5%. The glutaraldehyde treatment is not used to bring about any improvement in the operational stability of the preparation. It is incorporated into the process to induce formation of more uniform gel particles by imparting more rigidity to the bacterial cells.

When the whole cell enzyme is treated with glutaraldehyde activity losses occur that increase as the glutaraldehyde concentration is increased. We have discovered that the incorporation of 0.005 to 0.05% cobaltous ion, preferably 0.025%, based on the weight of the dry whole cells, significantly reduces this activity loss, which results from reagent inactivation. The effects of cobalt on glutaraldehyde treatment are shown in Table I.

TABLE I

EFFECT OF COBALT ON RETENTION OF ACTIVITY OF GLUTARALDEHYDE TREATED GEL ENTRAPPED ENZYME

| | Percent Activity Retained | |
|---|---|---|
| Percent Glutaraldehyde | No Cobalt Added To Preparation | 250–500 ppm Cobalt Added To Preparation |
| 0 | 100 | |
| 1 | 99 | 103 |
| 2 | 90 | 97 |
| 5 | 69 | 83 |
| 10 | 26 | 40 |
| 25 | 22 | |

Table II shows that glutaraldehyde-cobaltous ion-treated enzyme-agar gel particles of the present invention display 89% of the available activity when operating on a non-cobalt-containing glucose substrate. When cobalt is not used in the gel particles, a considerably lower amount (72%) of the activity is displayed in a non-cobalt-containing glucose substrate. Thus, it can be seen that the inclusion of cobaltous ion in the enzyme-agar gel particles enhances the available activity of the entrapped enzyme.

TABLE II

EFFECT OF COBALT ON AVAILABLE ACTIVITY OF ENTRAPPED ENZYMES

| Percent Cobalt in Particle | Percent Available Activity | |
|---|---|---|
| (Based on Whole Cell Weight) | Substrate With $3 \times 10^{-4} M\ Co^{++}$ | Substrate With no $Co^{++}$ |
| 0.0 | 100 | 72 |
| 0.025[1] | 100 | 89 |

[1] Enzyme has been treated with 5% glutaraldehyde.

EXAMPLE I

One gram of commercial USP agar was dissolved in 25 ml of boiling water with agitation. The agar solution was then cooled and maintained at 53° C. One gram of dry whole cells of *Actinoplanes missouriensis* NRRL B-3342 was suspended in 25 ml water at ambient temperature, then added to the agar solution and mixed. The pH of this mixture ranged from 7.0 to 7.5. Spherical particles were then formed by injecting the warm mixture into a solvent mixture of ethyl acetate and ethylene dichloride. The solvent mixture comprised 3 parts ethyl acetate and 1 part ethylene dichloride, and the mixture was maintained at a temperature of 10° C. to 15° C. After decanting the solvent the spherical particles were washed with 500 ml of water. The beads were then dried to a moisture content of 6.9% (w/w) and assayed at 1,171 IGIU/g.[2]

[2] IGIU: International Glucose Isomerase Unit—that amount that will convert 1 micromole of glucose of fructose per minute under standard assay conditions (pH: 7.5; temperature 65° C.; magnesium: 0.007 M).

Duplicate portions of dried particles, 0.2812 g. (dry solids) were swollen with dextrose substrate at about 60° C. for 2 hours. One substrate, comprising 45% solids (weight), contained $7 \times 10^{-3}$ M $Mg^{++}$ and 0.025% $SO_2$ (dsb). The other substrate contained an additional $3 \times 10^{-4}$ M $Co^{++}$. The pH of each was adjusted to 7.5.

The swollen particles were packed into $1.6 \times 20$ cm jacketed columns and maintained at 65° C. Prior to addition to the columns, the active particles were diluted with agar particles containing no enzyme to give a bed volume of about 18 ml.

The substrate was pumped continuously through a heat exchanger at 65°–67° C. into the bottom of the column at a flow rate of 11.3 ml/hr.

The results are summarized in Table III:

TABLE III

| | Substrate Containing No Additional Cobalt | | Substrate Containing $3 \times 10^{-4} M\ Co^{++}$ | |
|---|---|---|---|---|
| Hours | Percent Fructose Produced | Activity (IGIU/g) | Percent Fructose Produced | Activity (IGIU/g) |
| Initial | 28.4 | 941 | 35.4 | 1312 |
| 240 | 26.7 | 856 | 30.7 | 1067 |
| 480 | 20.9 | 601 | 26.0 | 823 |
| 576 | 17.2 | 468 | 20.9 | 607 |

[1] The level of fructose produced is low due to the brief time of contact.

EXAMPLE 2

The agar solution was prepared as described in Example 1. To an enzyme suspension as described in Example 1 was added 0.025% cobaltous ion as $CoCl_2 \cdot 6H_2O$ (dry cell weight basis). The resulting solution was then mixed. To the same suspension was added 5% of the bifunctional alkyl reagent, glutaraldehyde, as a 25% aqueous solution. The suspension was stirred and allowed to react for 30 minutes at ambient temperature. This mixture was then added to the agar solution and mixed. The gel particles were then formed, washed and dried as in Example 1.

Duplicate portions of the dried particles were swollen in dextrose substrate as described in Example 1 and packed in a $1.6 \times 20$ cm jacketed glass column heated at 65° C. Dextrose substrates as described in Example 1 were passed through the column continuously at a flow rate of about 11.8 ml per hr. The pH of the substrate was kept at 7.5.

The results are summarized in Table IV:

TABLE IV

| | Substrate Containing No Additional Cobalt | | Substrate Containing $3 \times 30^{-4} M\ Co^{++}$ | |
|---|---|---|---|---|
| Hours | Percent Fructose Produced | Activity (IGIU/g) | Percent Fructose Produced | Activity (IGIU/g) |
| Initial | 41.9 | 1369 | 44.1 | 1540 |
| 120 | 39.2 | 1150 | 42.4 | 1370 |
| 240 | 38.0 | 1073 | 41.3 | 1261 |
| 360 | 34.1 | 862 | 39.4 | 1118 |
| 480 | 30.0 | 701 | 36.4 | 954 |

EXAMPLE 3

To a whole cell enzyme suspension as described in Example 1 was added 0.025% cobaltous ion in the form of cobalt chloride. The suspension was then added to an agar solution, stirred, and the gel particles were formed, washed, and dried as in Example 1.

A portion of the gel particles were swollen in a glucose substrate and packed into a column at 65° C. A glucose substrate containing 0.007 M $Mg^{++}$ and no cobalt was continuously pumped through the column at a flow rate of 9.6 ml per hr. The initial activity level was 1246 IGIU/g and after six days, the level had fallen to 968 IGIU/g.

EXAMPLE 4

Dried whole cell enzyme (0.5 g) was suspended in 12.5 ml of water at ambient temperature and then stirred; thereupon 0.025% cobaltous ion was added in the form of cobalt chloride. Glutaraldehyde at a level of 5% of dry cell weight was added and allowed to react for 30 minutes. The resulting suspension was added to a dissolved agar solution and mixed. The agar solution was maintained at 50° C. to 55° C. The gel particles were formed by injecting and agar/enzyme solution into an ethyl acetate solution with stirring. The ethyl acetate had been kept at 5°-12° C. The solvent was decanted, and the gel particles were washed and dried as in Example 1. The material was assayed at 1100 IGI-U/g.

What is claimed is:

1. A process of immobilizing glucose isomerase comprising the steps of:
   A. Mixing 0.5 to 1.5 parts by weight whole microbial cells containing glucose isomerase with one part by weight of agar,
   B. Combining the agar-microbial cell mixture with organic solvent,
   C. Recovering discrete particles of agar gel with whole microbial cells containing glucose isomerase dispersed therethrough, and
   D. Drying the particles to a moisture level of less than about 15%.

2. The process of claim 1 wherein the ratio of whole microbial cells containing glucose isomerase to agar is about 1 to 1 by weight.

3. The process of claim 1 wherein said organic solvent is a mixture of ethyl acetate and ethylene dichloride.

4. The process of claim 3 wherein the ratio of ethyl acetate to ethylene dichloride is 3 to 1.

5. The process of claim 1 wherein said organic solvent is ethyl acetate.

6. The process of claim 1 wherein the organic solvent is at a temperature of between 5° C. and 15° C. when the agar-enzyme mix is combined therewith.

7. The process of claim 1 wherein the particles are substantially spherical in shape.

8. The process of claim 1 wherein said organic solvent is butyl acetate.

* * * * *

UNITED STATES PATENT AND TRADEMARK OFFICE
CERTIFICATE OF CORRECTION

PATENT NO. : 4,208,482
DATED : June 17, 1980
INVENTOR(S) : Irving Ehrenthal and Keith E. Miner It is certified that error appears in the above-identified patent and that said Letters Patent are hereby corrected as shown below:

Column 5, line 57, footnote number 2, after the word glucose, "of" should be ---to---; footnote number 2 should be at the bottom of the page.

Column 6, line 10, under the heading Table III, the first occurence of "Produced" should be ---Produced$^1$---.

Column 6, line 41, under the heading Table IV, "3 x $30^{-4}$M $Co^{++}$" should be ---3 x $10^{-4}$M $Co^{++}$---.

Signed and Sealed this

Twenty-third Day of September 1980

[SEAL]

Attest:

SIDNEY A. DIAMOND

Attesting Officer

Commissioner of Patents and Trademarks